United States Patent [19]

Fiato et al.

[11] Patent Number: 4,749,677

[45] Date of Patent: Jun. 7, 1988

[54] PROCESS FOR THE PREPARATION OF SLURRIED CO HYDROGENATION CATALYSTS

[75] Inventors: Rocco A. Fiato, Scotch Plains; Sabato Miseo, Pittstown, both of N.J.

[73] Assignee: Exxon Research and Engineering Company, Florham Park, N.J.

[21] Appl. No.: 923,194

[22] Filed: Oct. 27, 1986

Related U.S. Application Data

[63] Continuation-in-part of Ser. No. 808,025, Dec. 12, 1985, abandoned.

[51] Int. Cl.$^4$ .......................... B01J 21/06; B01J 23/46
[52] U.S. Cl. ..................................... 502/325; 518/715
[58] Field of Search ................. 502/174, 325; 518/715

[56] References Cited

U.S. PATENT DOCUMENTS 4,042,614  8/1977  Vannice et al. ................. 502/325 X
4,619,910 10/1986  Dyer et al. ....................... 502/325 X

*Primary Examiner*—W. J. Shine
*Attorney, Agent, or Firm*—Richard E. Nanfeldt

[57] ABSTRACT

A process for forming a catalyst composition produced by the steps of:

(a) adding to a stirred reactor $TiO_2$, a ruthenium carbonyl complex and an inert alkane hydrocarbon;
(b) adding a gas mixture of $N_2$:CO to said slurry reactor;
(c) adding a gas mixture of $N_2$:$H_2$ to said slurry reactor; and
(d) increasing the temperature of said slurry reactor from about 20° C. to about 250° C. and the pressure of said slurry reactor from about 1 to about 20 atm for about 2 to about 6 hours to cause the decomposition of said ruthenium carbonyl complex to form said slurry catalyst composition.

2 Claims, No Drawings

PROCESS FOR THE PREPARATION OF SLURRIED CO HYDROGENATION CATALYSTS

CROSS-REFERENCE TO RELATED APPLICATION

This application is a continuation-in-part of U.S. Ser. No. 808,025, filed Dec. 12, 1985, now abandoned.

BACKGROUND OF THE INVENTION

1. Field of the Invention

This invention relates to the preparation of slurry metal catalysts useful in Fischer-Tropsch synthesis by the in situ decomposition of Group VIII metal carbonyls in the presence of hydrothermally stable metal oxides.

2. Brief Description of the Prior Art

A number of catalyst systems have been prepared by in situ decomposition of various Group VIII metal carbonyl complexes, alone or in the presence of various support materials, i.e., H. Schultz in *New Synthesis with Carbon Monoxide*, J. Falbe, Ed., Springer Verlag, Berlin (1980).

However, these studies have failed to establish or identify the effects and ultimate influence of the support on catalyst properties. They have frequently employed rather severe conditions, i.e., elevated temperatures and/or pressures to achieve the required carbonyl decomposition step. These conditions can, in many cases, adversely affect catalyst performance due to undesired sintering, agglomeration or deposition of the metal on the support material in an uncontrolled way.

McVicker and Vannice described the production of potassium Group VII metal Fischer-Tropsch catalysts by impregnation of $Al_2O_3$ or $SiO_2$ with potassium Group VIII metal carbonyl complexes in *J. Catalysis*, 63, 25 (1980). Their catalysts were prepared ex situ with a high temperature (350° C.) vacuum drying, followed by a 500° C. $H_2$ treatment to activate the material.

Smith and coworkers in *J. Amer. Chem. Soc.* 100, 2590 (1978) have described a procedure for production of supported Group VIII metal catalysts by decomposition of metal carbonyl complexes on $Al_2O_3$. They indicated that these catalysts are active for conversion of $CO/H_2$ to methane and that if the carbonyl decomposition step was performed in a $CO/H_2$ containing gas that methane was formed.

Tatsumi and coworkers recently reported that zeolite entrapped ruthenium carbonyl clusters are active for Fischer-Tropsch synthesis, *J. C. S. Chem. Comm.*, page 207 (1985). Their catalysts were prepared by ex-situ procedures involving vacuum drying of the zeolite at 400° C., impregnation at 120° C., followed by activation at 200° C. in $H_2$ or $N_2$. Their catalyst when tested with a 1:1$H_2$:CO feed generated a Fischer-Tropsch product mixture rich in $C_1-C_4$ hydrocarbons.

Madon has recently disclosed, in U.S. Pat. No. 4,477,595, the use of supported ruthenium catalysts for the production of liquid hydrocarbons from $CO/H_2$. The catalysts useful in this process were prepared from $RuCl_3$ or $Ru(NO_3)_3$ and were activated at 400°–450° C. in flowing $H_2$ before use.

In none of the above examples is there described a procedure for generating an active supported ruthenium catalyst for the selective synthesis of liquid hydrocarbons under slurry reactor conditions.

F. Bellstedt, in Dissertation, Karlsruhe (1971), has described the preparation of slurried ruthenium catalysts by in situ decomposition of $Ru_3CO_{12}$ at 100° to 150° C. and 50 to 100 bar. Supports such as kieselguhr, active carbon, aluminum oxide and ruthenium (IV) oxide were employed.

However, we have successfully attempted to prepare an analogous active catalyst via decomposition of $Ru_3CO_{12}$ at 200° to 220° C. and 1 to 2 bar $H_2$. The catalyst exhibited only marginal CO hydrogenation activity over a 16-hour operating period. In addition, the reaction mixture which was discharged from the reactor contained detectable quantities of the precursor complex, $Ru_3CO_{12}$, indicating that the decomposition step did not proceed to complete conversion.

SUMMARY OF THE INVENTION

The present invention teaches the formation of a slurry catalyst composition by using a Degussa $TiO_2$ (P-25), which had been pretreated with 10% $H_2$/90% He at 450° C. for several hours and adding to the $TiO_2$ the reaction mixture before the carbonyl decomposition step. This results in a catalyst which is highly active and selective for production of liquid hydrocarbons, i.e., ca. 40 to 60% conversion at 240° C., 100 sccm of 6:3:1$H_2$:CO:$N_2$, 0.4 to 0.6 MPa, 600 rpm, with a product distribution characterized by a Flory alpha of 0.80.

Further, it is contemplated within the spirit of the instant invention that a variety of metal oxides, e.g., $Nb_2O_5$, $V_2O_5$, MgO, $ZrO_2$, $CeO_2$, $MnO_2$, CuO, ZnO, $Cr_2O_3$, $SiO_2$, will function in a similar fashion. These materials may serve as effective nucleation agents, facilitate carbonyl decomposition, and/or serve as relatively stable supports for a number of catalysts derived from Group VIII metal based carbonyl complexes.

The preparation of highly active slurried CO hydrogenation catalysts can be achieved by in situ decomposition of selected metal carbonyl complexes in the presence of hydrothermally stable metal oxides. This procedure eliminates the need for high pressures and/or temperatures which are frequently required with conventional catalysts and, with the appropriate metal oxide, gives a catalyst which is highly active and stable to normal CO hydrogenation reaction conditions.

The catalyst preparation procedure is achieved directly in the reactor employed in the Fischer-Tropsch synthesis. The system is charged with the ruthenium carbonyl complex, e.g., $Ru_3(CO)_{12}$, the pretreated metal oxide support, an inert organic solvent and a CO-containing gas to purge the system and to stabilize the complex during the initial heat-up. The system is then heated to a temperature $\leq 100°$ C. and the system is purged with $H_2$ in a diluent gas, such as nitrogen, argon or helium. The temperature is then gradually increased to $\leq 250°$ C. in flowing $H_2$ and maintained at these conditions for 1 to 2 hours. At the end of this period the catalyst is ready for use in Fischer-Tropsch synthesis.

The synthesis reaction is conducted in a continuously stirred tank reactor, although other types of slurry bubble column reactors could also be used. The synthesis step is conducted at elevated temperatures, usually less than 270° C., preferably between 230°–250° C. The system is fed a mixture of $H_2/CO$ alone or in the presence of a diluent gas, such as nitrogen, argon or helium. The $H_2/CO$ feed ratio can be varied from 5/1 to 1/5 and is preferably maintained at 1/1 to 2/1. The synthesis reaction is conducted at elevated pressures in the range of 2-30 atmospheres and preferably in the range of 4-20 atmospheres. The synthesis reaction is conducted in an inert organic solvent with catalyst present at the 1-20% weight level, preferably at 5-15% weight level. The solvent employed consists of a high boiling hydrocarbon which is inert to the reaction environment. Hydrocarbons containing more than 15, and preferably more than 25, carbon atoms are preferred. Commercially available high molecular weight paraffins, such as hexadecane or octacosane, or high molecular weight paraffins generated in the synthesis reaction are well suited for this use.

The process of the instant invention comprises the steps of: adding $Ru_3(CO)_{12}$, $TiO_2$ and an inert alkane to a stirred slurry reactor; adding a gas mixture of $CO:N_2$ to the slurry reactor; adding a gas mixture of $H_2:N_2$; increasing the temperature and pressure of the slurry reactor and maintaining said temperature and pressure for a sufficient period of time to decompose the $Ru_3(CO)_{12}$ to form a Ru catalyst system supported on $TiO_2$; adding to the slurry reactor a feed of a gas mixture of $H_2:CO:N_2$; and maintaining temperature and time to form liquid hydrocarbons from said CO and $H_2$.

The process for forming the slurry catalyst composition is generally described by the steps of adding to a stirred slurry reactor $TiO_2$, ruthenium carbonyl complex and an inert alkane hydrocarbon; sealing said stirred slurry reactor and adding a gas mixture of $N_2:CO$ at room temperature and one atmospheric pressure to said stirred slurry reactor to purge said stirred slurry reactor; heating said stirred slurry reactor to about 100° C. and raising the pressure of said stirred slurry reactor to about 4 to about 10 atmospheres and adding a gas mixture of $N_2:H_2$ to said stirred slurry reactor; and increasing the temperature of said stirred slurry reactor to about 230° C. to about 270° and the pressure of said stirred slurry reactor from about 4 to about 20 atm for about 2 to about 6 hours to cause the decomposition of said ruthenium carbonyl complex to form said slurry catalyst composition.

The slurry catalyst composition comprises $TiO_2$; and the decomposition product of a ruthenium carbonyl complex which is $Ru_3(CO)_{12}$, said decomposition product being formed by the decomposition of said $Ru_3(CO)_{12}$ in the presence of a gas mixture of $CO:H_2:N_2$ at a temperature of about 230° C. to about 270° C. and a pressure of about 4 to about 20 atm for a sufficient period of time to form said decomposition product, said decomposition product being supported on said $TiO_2$.

DESCRIPTION OF THE INVENTION AND PREFERRED EMBODIMENTS

Relatively mild conditions can be successfully employed to achieve the required carbonyl decomposition step if selected metal oxides are incorporated in the reaction mixture. These materials serve not only as nucleation sites, but also with the appropriate pretreatment can facilitate the carbonyl decomposition step.

The following Examples illustrate the best mode of the invention as contemplated by use and should not be construed as being limitations on the scope and spirit of the instant invention.

EXAMPLE 1

Catalyst Preparation

An unsupported ruthenium catalyst was prepared via decomposition of $Ru_3CO_{12}$ at 20° to 240° C. and 1 to 10 atm $H_2$ in a 300 cc Parr continuous tank reactor (CSTR).

The reactor was charged with a mixture of 50 grams of octacosane and 0.25 grams of $Ru_3(CO)_{12}$. The system was then sealed and purged with a 3:1 mixture of $CO:N_2$ at room temperature and the pressure then raised to 10 atmospheres. The reactor was heated to 100° C. and a 6:1$H_2:N_2$ gas mixture was fed at 70 sccm. The pressure on the system was adjusted to 4 atmospheres and the temperature increased to 200° C. over a one and one-half hour period.

After an additional one hour period at the 200° C. pretreatment conditions a feed of $H_2:CO:N_2$ at 60:30:10 sccm was introduced and the temperature then increased to 240° C.

The off-gas from the reactor was monitored with a refinery gas analyzer to determine the level of CO conversion and the distribution of products obtained from the reaction of CO and $H_2$.

The catalyst exhibited marginal CO hydrogenation activity over a 16-hour operating period. In addition, the reaction mixture which was discharged from the reactor contained detectable quantities of the precursor complex, $Ru_3(CO)_{12}$, indicating that the decomposition step did not proceed to complete conversion.

EXAMPLE 2

Using the apparatus, pretreatment procedure and general $CO/H_2$ run variables described above in Example 1, an identical experiment was conducted in which Degussa $TiO_2$ (P-25) which had been pretreated with 10% $H_2$/90% He at 450° C. for several hours was added to the reaction mixture before the carbonyl decomposition step. The catalyst prepared by this procedure was highly active and selective for production of liquid hydrocarbons, i.e., ca. 40 to 60% CO conversion at 240° C., 100 sccm of 6:3:1$H_2:CO:N_2$, 4 to 6 atmospheres, 600 rpm, with a product distribution characterized by a Flory alpha of 0.80.

EXAMPLE 3

A 300 cc Parr CSTR was charged with 5.0 g of 1% Ru/$TiO_2$, runs 1 and 2, or an equivalent amount of metal oxide support and $Ru_3CO_{12}$ to give an equivalent loading of active metal in 50 g of octacosane solvent, runs 3 to 6. The system was purged with CO and then pressurized with $H_2$ to 100 psig for 2 hours to prereduce the catalyst at 220/°C. Feed gas was then introduced to the system: $H_2$ at 60 sccm, CO at 30 sccm and $N_2$ at 10 sccm, to achieve and SHSV of 1,200 V/V/cat/hr. based on an assumed 5.0 cc dry catalyst volume charge and the total pressure adjusted to 6 atmospheres. The feed gas and off-gas streams were monitored with an HP-5840A Refinery Gas Analyzer to determine the extent of CO conversion and the nature of $C_{1+}$ products. Results are given below in the Table.

TABLE

Performance of Slurried CO Hydrogenation Catalysts

| Catalyst | Run | Temp. °C. | % CO Conversion | $CO_2$ | $CH_4$ | $C_2-C_4$ | $C_{5+}$ |
|---|---|---|---|---|---|---|---|
| Conventional | | | | | | | |

TABLE-continued
Performance of Slurried CO Hydrogenation Catalysts

| Catalyst | Run | Temp. °C. | % CO Conversion | Wt. % Selectivity | | | |
|---|---|---|---|---|---|---|---|
| | | | | $CO_2$ | $CH_4$ | $C_2$-$C_4$ | $C_{5+}$ |
| 1% Ru/$TiO_2$ | (1) | 250+ | 49 | 3.2 | 14.4 | 8.9 | 7.35 |
| | (2) | 260 § | 10 | 2.0 | 20.0 | 30.0 | 48.0 |
| Carbonyl Based*§ | | | | | | | |
| Ru | (3) | 260 | 15 | tr | 4.7 | 19.5 | 75.8 |
| Ru/$CeO_2$ | (4) | 240 | <5 | Nil | NA | NA | NA |
| Ru/$Al_2O_3$ | (5) | 240 | 25 | 3.0 | 19.3 | 9.4 | 68.3 |
| Ru/$TiO_2$ | (6) | 240 | 55 | 6.7 | 12.3 | 17.5 | 63.5 |

Conditions: 2:1 $H_2$:CO, 1,200 V/V/ cat/hr, 6 atmospheres + 450° C. pre-reduction
§ no 450° C. pre-reduction
*1% metal loading or equivalent Catalysts derived from in situ decomposition of $Ru_3(CO)_{12}$, runs 3 to 6, exhibit a wide range of activities in the conversion of CO/$H_2$ to hydrocarbons. The $TiO_2$ supported system, run 6, exhibits better activity than an equally treated conventional analog, run 2, or conventional analog that was pre-reduced with $H_2$ at 450° C. prior to charging the Parr reactor. The carbonyl based catalyst in run 6 also generates less $CH_4$ than either of the conventional analogs.

The carbonyl based catalyst can be prepared from commercially available $Ru_3(CO)_{12}$ or from carbonyl complexes that are formed at relatively low temperatures, <230° C., and high pressures, >150 psig, encountered with use of conventional ruthenium based catalysts. In the latter case, this would provide a method for recycling spent ruthenium from conventional catalysts.

What is claimed is:

1. A process for forming a slurry catalyst composition produced by the steps of:

(a) adding to a stirred slurry reactor $TiO_2$, ruthenium carbonyl complex and an inert alkane hydrocarbon;
   (b) sealing said stirred slurry reactor and adding a gas mixture of $N_2$:CO at room temperature and one atmospheric pressure to said stirred slurry reactor to purge said stirred slurry reactor;
   (c) heating said stirred slurry reactor to about 100° C. and raising the pressure of said stirred slurry reactor to about 4 to about 10 atmospheres and adding a gas mixture of $N_2$:$H_2$ to said stirred slurry reactor; and
   (d) increasing the temperature of said stirred slurry reactor to about 230° F. to about 270° and the pressure of said stirred slurry reactor from about 4 to about 20 atmospheres for about 2 to about 6 hours to cause the decomposition of said ruthenium carbonyl complex to form said slurry catalyst composition.

2. A process according to claim 1 wherein said ruthenium carbonyl complex is $Ru_3(CO)_{12}$.

* * * * *